United States Patent [19]

Smith

[11] Patent Number: 5,674,261

[45] Date of Patent: Oct. 7, 1997

[54] S-SHAPED ELECTROTHERAPY MASSAGE STICK

[76] Inventor: Cleveland S. Smith, 408 Thadral Point, Hot Springs, Ak. 71913

[21] Appl. No.: 626,491

[22] Filed: Apr. 3, 1996

[51] Int. Cl.$^6$ .................. A61N 1/26; A61N 1/18
[52] U.S. Cl. .................. 607/46; 607/66; 607/72; 607/148
[58] Field of Search .................. 607/2, 46, 48, 607/63, 66, 72, 75, 76, 148; 128/907

[56] References Cited

U.S. PATENT DOCUMENTS

| 397,474 | 2/1889 | Stanley | 607/148 |
|---|---|---|---|
| 676,604 | 6/1901 | Fritze | 607/148 |
| 3,403,684 | 10/1968 | Stiebez et al. | 607/72 |
| 4,319,584 | 3/1982 | McCall | 607/72 |
| 4,509,521 | 4/1985 | Barry | 607/46 |
| 4,694,840 | 9/1987 | Kairis et al. | 607/72 |
| 4,763,657 | 8/1988 | Chen et al. | 607/3 |
| 4,962,766 | 10/1990 | Herzon | 607/66 |
| 5,207,231 | 5/1993 | Fakhri | 607/63 |

OTHER PUBLICATIONS

Brochure, *Deep Muscle Massage Instruments*, Pressure Positive Company (1995).
Focus Brochure, *Protocol for the Treatment of Muscle Spasm in the Back and Neck*, Empi, Inc. (1989).
Instruction Manual, *Solitens Compact electro-therapeutic device* (1991).

*Primary Examiner*—William E. Kamm
*Assistant Examiner*—Carl H. Layno
*Attorney, Agent, or Firm*—Hill, Steadman & Simpson

[57] ABSTRACT

An electrotherapy device is capable of a person independently, simultaneously locating the most appropriate and effective treatment sites before administering electrotherapy and massage for acute and chronic pain. A stiff elongated support member has an electrical conductor/physical stimulator attached to an arcuate distal end. The electrical conductor/physical stimulator is attached to an electric signal generator for providing electrotherapy signals while a patient simultaneously massages a point on the patient's body with the electrical conductor/physical stimulator. The device also provides the user the ability to locate the most appropriate treatment sites for providing relief of their symptoms.

15 Claims, 3 Drawing Sheets

S-SHAPED ELECTROTHERAPY MASSAGE STICK

BACKGROUND OF THE INVENTION

1. Field of the Invention

The present invention relates generally to the field of therapeutic devices for relieving pain and other ailments, and more particularly, the present invention relates to an improved therapy device which is capable of simultaneously providing physical stimulation and massage as well as electrotherapy.

2. Description of the Related Art

A large number of people suffer from acute and chronic pain resulting from back and neck injuries and other types of trauma. Even greater numbers suffer from other ailments such as arthritis. Existing therapies for treatment of these conditions include the use of acupuncture and physical stimulation through massage. An alternate form of treatment is electrotherapy wherein electrical impulses are used to stimulate nerves and muscles and provide relief from pain. A variety of devices are currently used for providing these known forms of treatment.

In one device, physical massage is provided through a stiff structure which allows the patient to massage various portions of his or her own body. One particular embodiment of this device is the Theracane® manufactured by Pro Massage Co. of Denver, Colo. In this device, the physical stimulator is an elongated member having various fixed protrusions along its length. The elongated member has an arcuate extension at one end. The fixed protrusions may be used either for gripping the Theracane® device in order to apply pressure or as a means through which stimulation may occur. An individual is able to use this device to provide physical stimulation and massage. The arcuate shape of the device allows the patient to independently reach any portion of the body with a normal range of motion. While this device is somewhat useful and provides satisfactory results, it is nevertheless limited in that it is only capable of providing physical stimulation through massage.

In another form of treatment for acute and chronic pain, electrotherapy is employed to relieve pain. In electrotherapy, electrodes are placed at various locations on the patient's body and electrical impulses are transmitted from one electrode to another through the patient's body. This electrical stimulation provides relief from acute and chronic pain. The electrical impulses are typically either bi-phasic symmetrical square waves or bi-phasic asymmetrical waves. In existing treatments of this type, the electrodes are typically physically secured to the body via tape or some other known type of conductor. Wires which travel from the electrodes are attached to a electrical signal generator which provides the electrical impulses for stimulation. The electrical signal generator is able to provide a variety of electrical impulses that vary in both magnitude and duration. This alternate form of therapy provides an additional mechanism through which those who suffer acute or chronic pain may receive relief.

While electrotherapy treatment also provides satisfactory results in the treatment of acute and chronic pain, several drawbacks exist with this device. Most notably, an individual user is unable to independently attach the electrodes satisfactorily to any location on the body. Specifically, one area in which individuals typically encounter difficulty in the placement of these devices is the back. Unfortunately, this location is often one in which patients require treatment for acute and chronic pain. With these known devices, placement in such a location requires the assistance of another person. This significantly reduces the ability to use the device independently and, as a result, the device is less desirable.

It has been recognized that a variety of treatment is most successful in helping patients to overcome acute and chronic pain. For example, while many patients respond to both electrotherapy and physical stimulation when they are provided independently, improved results from treatments are achieved when both forms of treatment are applied simultaneously or alternately during a single treatment session. Currently, no known device is capable of simultaneously providing multiple forms of treatment for patients suffering from acute or chronic pain or alternately providing different forms of treatment. All known devices for the treatment of acute and chronic pain require patients to alternately receive each form of treatment from a trained professional.

It has also been recognized that electrotherapy is most effective when the site of electrical stimulation is varied. This results in another drawback to these known devices in that movement of the electrodes requires that a person detach and then re-secure the electrodes in another location. This adds to the time that it takes for completion of the treatment because much time is simply wasted in moving and securing electrodes. Furthermore, it is often very difficult for an individual to conveniently move the electrodes to various places on the person's own body in order to vary the site of electrical stimulation. This is especially true because many times the desired site of electrical stimulation is in a difficult place to reach such as the individual's back.

While each of the above mechanisms may provide satisfactory results, as noted, they are inherently limited. Thus, a need exists in the art for a device which is capable of providing therapy for individuals with acute or chronic pain conditions that simultaneously provides alternate forms of treatment. There is also a need in the art for a device which is capable of simultaneously and alternately providing varied forms of stimulation which is also easily used by an individual independently.

SUMMARY OF THE INVENTION

The present invention provides a mechanism for treating acute and chronic pain that is capable of simultaneously providing alternate forms of treatment. Most significantly, the present invention is a device capable of simultaneously providing both electrotherapy and physical stimulation from a single unit which an individual may independently operate. This device incorporates an elongated arcuate member having wires located internally for transmitting electrical impulses to one or more exposed electrical conductors. The electrical conductors transmit electrical impulses into the body of a person undergoing treatment. The electrical conductors are formed from a substantially stiff material which may alternately or simultaneously be used for providing physical stimulation in a desired area along with the electrotherapy. The elongated member has at least one arcuate end that is capable of positioning the electrical conductors conveniently at various locations of the person's body, including difficult to reach areas such as an individual's back. The arcuate shape allows an individual to independently position the tip of the electrotherapy device wherever needed.

In a preferred embodiment of the present invention, three electrical conductors are attached to an end of the elongated member. The electrical conductors are located at each end of a three-pronged member and the electrical conductors are electrically insulated from one another. Separate wires are located within the elongated member and connect each of the electrical conductors to a contact point located on the elongated member. The elongated member is known as an electrotherapy device and provides a path for electrical wires to connect the electrical conductors to separate ports of an electrical generator.

The electrical generator provides electrical stimulus through the electrical conductors. The generator may provide a signal which is simultaneously provided to the three electrical conductors or the signal may be alternately switched to each of the individual conductors. A separate electrical connection to the person's body provides a return path for the electrical signals which are transmitted into an individual. This separate connection may be provided by a removable contact point which is secured to the person's body at a select location through tape or the like or as an adhesive electrode such as those manufactured by Empi Inc. of St. Paul, Minn. 55112.

In another alternate embodiment of the present invention, electrical impulses may be transmitted between the electrical conductors located at the end of the elongated member. This employs the use of multiple conductors located at the distal end of the elongated member. Two or three conductors would be most desirable for this application. In such a design, an additional signal return path would not be required, however, the electrical conductors would require a greater physical separation in order to provide the appropriate electrical stimulation.

A person is able to simultaneously provide electrical stimulation along with massage by grasping the elongated member and applying slight pressure to the desired location with the one or more electrical conductors located at the end of the elongated member. A person using the device is also able to select between simultaneously providing massage and electrotherapy or alternating between these individual forms of treatment. The conductor is thus also referred to as a conductor-physical stimulator.

Figures 3, 4:
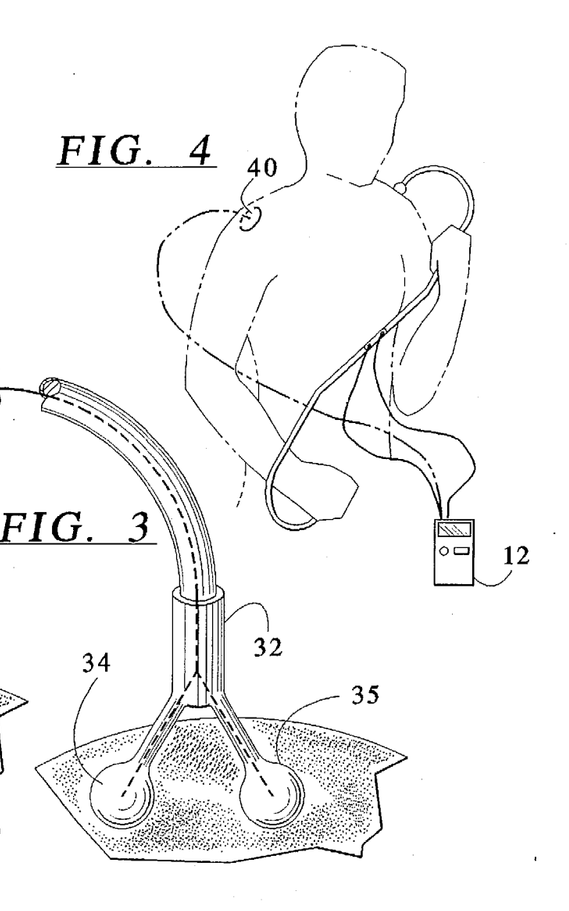
FIG. 3 illustrates an alternate embodiment of the attachment comprising two electrical conductor-physical stimulators.
FIG. 4 illustrates operation of the improved electro-therapy device of the present invention.

In a refined version of the present invention, the electrical conductor-physical stimulator is in the shape of a ball with a slight protrusion or knob extending from a side of the conductive ball. The protrusion is used in finding the most suitable location for applying electrical stimulation and physical massage treatment. Another conductor-physical stimulator is in the shape of a finger which has a coned appearance that narrows at its distal end. The distal end of this finger type probe is initially used in locating trigger points and then it is used in providing electrical stimulation to the desired locations. This attachment can also be used in the administration of physical stimulation (massage). In FIG. 4 the individual is shown grasping the opposite end of the electro-therapy device in order to provide a return path for the acupuncture/trigger point locating and stimulating electrical current for the generator. As an added feature, the electrical conductor-physical stimulator may incorporate a heating element to warm the conductor-physical stimulator. In such an embodiment, the electrical generator or an alternate power source would provide the energy for the heater.

It is known in the art that the most suitable site for treatment can be found by locating those areas which are more highly conductive than others. These sites are known as acupuncture points and they can be identified because of their low impedance characteristics. The protrusion on the first design of the conductor-physical stimulator or alternatively the distal end of the finger type probe is used as a probe and an electrical generator connected to the conductor applies a low-level electrical signal which is used in locating low impedance points on the person's body. When such a site is found, the generator provides an audible tone and the person then applies physical stimulation/massage and/or electrotherapy through the protrusion of the ball shaped electrode or the rounded portion of the finger tip shaped conductor/physical stimulator. A depressible button or other type of electric switch on the elongated member allows the person using the device to alternately select either a seek or stimulation mode.

The present invention also incorporates conductive covers for the electrical conductors to improve the transmission of the electrical signals into the desired locations of a persons body. These novel conductor covers include formed conductive sponges which are soaked with a conductive liquid and wrapped around the electrical conductor to improve the transmission qualities of the signals transmitted into a person's body.

The device has numerous advantages over the known devices of the prior art. Most significantly, the improved device of the present invention allows individuals undergoing electrotherapy treatment to enjoy greater independence in receiving their treatment by allowing individuals to independently and simultaneously provide physical stimulation and electrotherapy treatment.

Another advantage of the present invention is that a single device locates acupuncture points or trigger points and is also capable of simultaneously providing electrotherapy and physical massage.

A further advantage of the present invention is that an electric signal generator may be programmed to provide a variety of electrical stimulation signals (i.e. varying pulse width, pulse per second, intensity, duration and waveform shape or type of current) while a patient is receiving massage.

The magnitude, frequency, and shape of the electrical signals provided by the generator may be varied and adjusted to provide the most effective electrical stimulation for treatment. Experimentation with a variety of waveforms will determine the most appropriate treatment for each type of injury.

These along with other objects and advantages of the present invention will become apparent from the following detailed description of the presently preferred embodiments in light of the drawings.

DETAILED DESCRIPTION OF THE PRESENTLY PREFERRED EMBODIMENTS

Figures 1, 2:
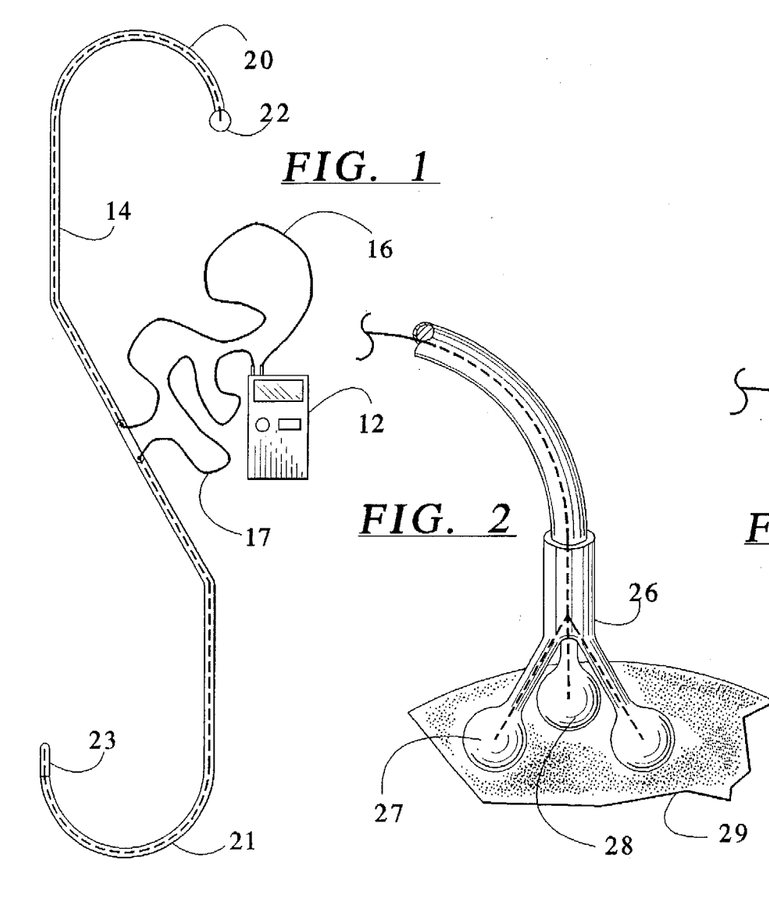
FIG. 1 illustrates a first embodiment of the present invention showing the elongated therapy device connected to an electrical impulse generator.
FIG. 2 shows an attachment for the end of the device which comprises three electrical conductor-physical stimulators.

FIG. 1 illustrates a first embodiment of the present invention. In this embodiment, an electrical impulse generator 12 is attached to the electrotherapy device 14 via lead wires 16 and 17. The electrotherapy device 14 comprises a strong stiff elongated member having hook shaped ends 20 and 21. One or more electrical conductor-physical stimulators 22,23 may be located at each end of the electrotherapy device 14 or only at a single end of the device. The arcuate or hook shaped ends 20, 21 allow an individual to independently place the electrical conductor-physical stimulator located at the distal end of the electrotherapy device 14 conveniently at any location on the body. The arcuate elongated electrotherapy device 14 is made of stiff material such as a hard plastic. The material is preferably electrically nonconductive. Understandably, it should be sufficiently strong and durable to provide physical massage to various parts of the body.

In a preferred embodiment of the present invention, the elongated member 14 is hollow and one or more wires (not shown for clarity) are located therein for transmitting electrical impulses from the generator 12 to an electrical conductor-physical stimulator 22 located at the end 20 of the elongated electrotherapy device 14. The electrical conductor-physical stimulator 22 of the elongated electrotherapy device 14 is an electrical conductor that transmits electrical impulses and is sufficiently strong to allow an individual to simultaneously provide massage with the device. At least one wire located within the elongated electrotherapy device 14 connects the electrical conductor-physical stimulator 22 to the electrical impulse generator 12 through the electrotherapy device 14. This is the most fundamental embodiment of the present invention. In this embodiment, an additional electrode may be attached to the person's body in order to provide a return path for the electrical impulses transmitted by the generator 12. A person using this device is able to physically massage a portion of the body while simultaneously providing electrical stimulation through the electrical conductor-physical stimulator 22. Additionally, the individual using the device may alternate between each form of treatment. The generator 12 may be programmed to provide a predetermined sequence of electrical impulses having varied magnitudes and waveforms. Alternatively, the generator 12 may provide a fixed type of waveform. The generator 12 may also be programmed to intermittently provide electrical stimulation during massage.

FIG. 2 illustrates an alternate embodiment of the present invention wherein the single electrical conductor-physical stimulator 22 of the embodiment shown in FIG. 1 is replaced by multiple electrical conductor-physical stimulator attachment 26. The attachment 26 provides three separate electrical conductor-physical stimulators 27, 28 and 29. The physical connection between the elongated member and the conductor portion of the conductor-physical stimulator is preferably somewhat flexible so that it allows one to physically stimulate while remaining in contact with the patient's skin. In this embodiment, preferably, each of the three electrical conductor-physical stimulators 27, 28 and 29 are connected to the electrical generator 12 with separate wires located within the elongated member 14. The separate connection of the individual electrical conductor-physical stimulators 27, 28 and 29 provides additional versatility for the unit. The generator 12 may provide a signal which is simultaneously applied to the three electrical conductor-physical stimulators 27, 28 and 29 or the signal may be alternately switched to each of the individual conductor-physical stimulators 27, 28 and 29.

As with the embodiment shown in FIG. 2, a separate electrical connection to the person's body provides a return path for the electrical signals. This separate connection may be provided by a removable contact point that is secured to the person's body at a select location through a self-adhesive electrode. The generator 12 may also transmit electrical impulses between the individual electrical conductor-physical stimulators 27, 28, and 29. In such a configuration, each of the conductor-physical stimulators 27, 28 and 29 would have independent connections to separate signal ports of the generator. The generator is thus able to switch the stimulation signal alternately between the separate conductors. Those conductors which are not connected to the stimulation signal at a particular time would provide the return path to the generator. In such a design, an additional signal return path to the generator 12 would not be required, however, the electrical conductor-physical stimulators would require a greater physical separation in order to provide the appropriate electrical stimulation. For example, if the electrical conductors are too close, the majority of the current will travel on the skin where the electrical conductors are placed. A separation of approximately 2 inches between the electrical conductors should provide satisfactory results so that sufficient electrical current will flow beneath the patient's skin.

In the embodiment of the invention illustrated in FIG. 2, the generator 12 may be programmed to provide electrical impulses of varying magnitude and form. Alternately, the generator 12 may provide electrical signals having homogenous magnitude and waveform.

FIG. 3 illustrates a further embodiment of the invention showing an electrical conductor attachment 32 which has two separate electrical conductor-physical stimulators 34 and 35. This embodiment of the invention operates in similar fashion to that illustrated in FIG. 2. In this embodiment, the generator may electrically connect each of the conductor-stimulators in order to simultaneously provide the electrical impulses, or alternatively, the generator may alternately transmit the impulses to each of the electrical conductor-stimulators independently. As noted above, the software which drives the generator will determine which type of signals will be generated. In either embodiment, the electrical conductor-physical stimulators would also incorporate a separate thermostatically controlled heater to warm the conductor. The electrodes are substantially spherical and have a preferred size of approximately 1⅛ inches in diameter or 3½ inches in circumference. The elongated member 14 preferably has a circumference of approximately 2½ inches.

FIG. 4 illustrates operation of the improved therapy device of the present invention. As noted above, the stimulation device of the present invention may be used to simultaneously provide electrotherapy treatment and physical massage. A return electrode 40 is attached at a convenient location such as at the shoulder as shown and electrical conductor-physical stimulators of the electrotherapy device are then placed at various locations which require treatment. The electrode 40 provides a return path for the electrical current. Alternately, a conductive pad on the opposite end of the electrotherapy device may provide the return path through the patient's hand as shown. The return path electrode could be a conventional skin placement electrode such as those manufactured by Empi Corporation of Minnesota. The larger the contact surface of the ground electrode, the more comfortable electrical stimulation will be. The electrical impulse generator 12 allows the individual to select timing and magnitude of the electrical impulses as prescribed by a trained health care professional. Alternately, as previously mentioned with the attachments shown in FIGS. 2 and 3, the individual may select various alternate forms of electrotherapy wherein electrical impulses are transmitted between the attached electrical conductor-stimulators or alternately from each of the attached electrical conductor-stimulators independently to the further attached electrode 40. The individual is thus able to simultaneously or alternately provide physical stimulation and electrotherapy to a desired location.

Figures 5, 6A, 6B, 7, 9:
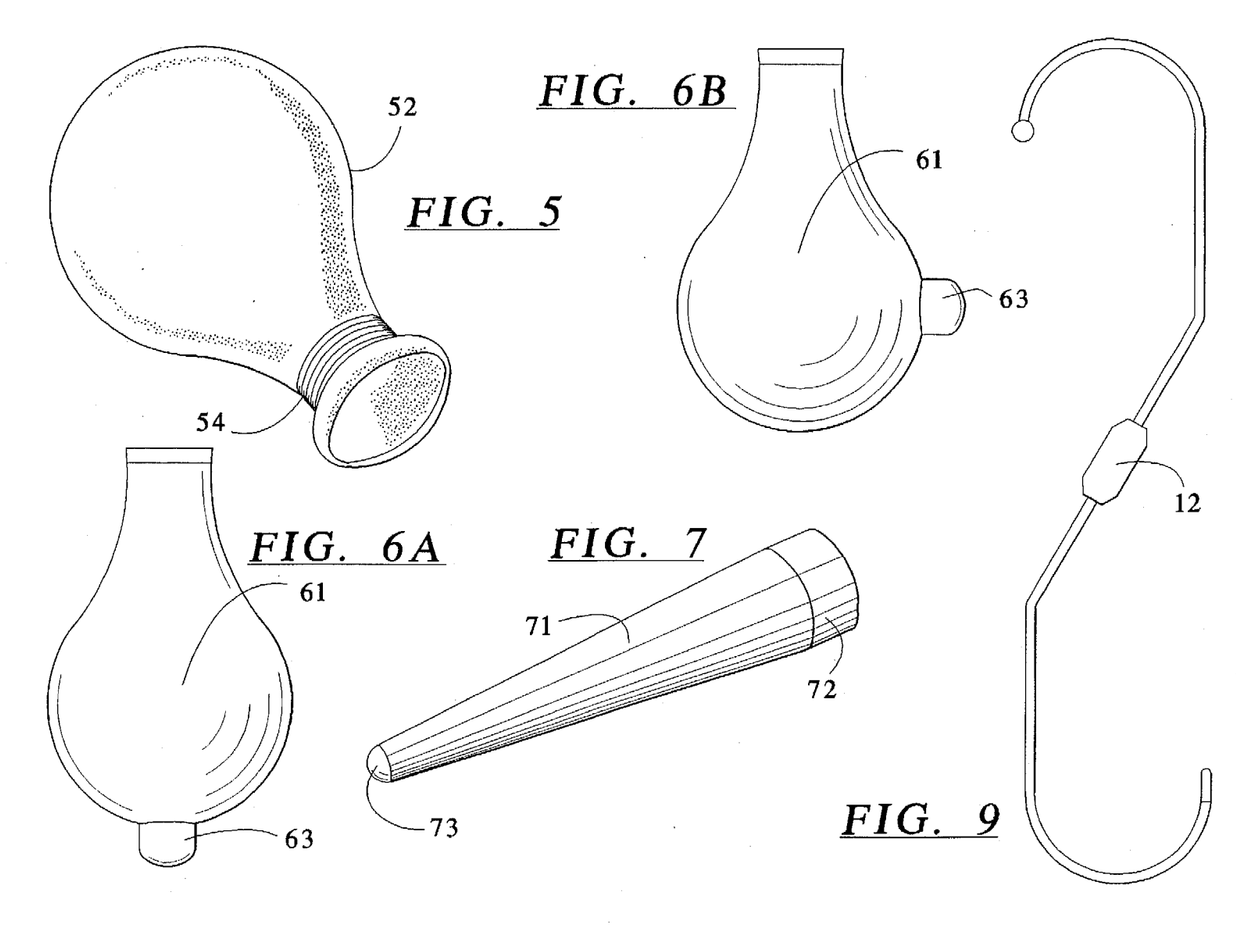
FIG. 5 illustrates a conductive cover for an electrical conductor of the electrotherapy device of the present invention which comprises a formed sponge which wraps around the electrical conductor of the electrotherapy device.
FIGS. 6A and 6B illustrate alternate embodiments of the electrical conductor-physical stimulator for use with the present invention.
FIG. 7 illustrates a further alternate embodiment of the conductor-physical stimulator for use with the present invention.
FIG. 9 illustrates the body of the elongated member of the present invention wherein an electric generator is incorporated into the body of the elongated member.

FIG. 5 illustrates a reusable electrode cover 52 for the electrical conductor-physical stimulator 22 of the electrotherapy device. In this embodiment, the cover 52 is a substantially elastic sponge material which is formed to substantially cover the electrical conductor-physical stimulator 22. An elastic strap 54 is bound around the base of the conductive material to secure the sponge onto the electrical conductor. This conductive sponge facilitates improved transmission of the electrical signal into the patient's body. Electrical conductivity and signal transmission is increased by placing the sponge in a saline or other ionic solution. The dampened sponge is then placed on a patient's skin.

The electrical generator 12 used with the present invention can be of a conventional design or one with enhanced capabilities. In the preferred embodiment, the electrical generator 12 will have intensity controls and timing controls for adjusting the electrical impulses which are accessible to the user. Alternately, these can be preprogrammed by a professional who designs a particular electrotherapy program for the user. In this regard, the electrical generator 12 can incorporate a memory cartridge which can be reprogrammed or alternately programmed to provide varying forms of stimulation to a user. The signal generator 12 has the capacity to send current to the acupuncture/trigger point locator or the opposite end of the invention which is programmed by the user.

After the most appropriate therapeutic current for stimulation is reached and developed through experimentation, then the signal generator that provides that chosen current can be embodied into the Stimucane or electrotherapy device of the present invention.

FIGS. 6A and 6B illustrate alternate embodiments of a first type of electrical conductor-physical stimulator for use with the present invention. The first embodiment of the electrical conductor-physical stimulator 61 of the present invention is comprised of a rounded ball conductor with a conductive protrusion 63. The electrical conductor-physical stimulator 61 is made of a stiff supportive structure having a conductive external shield or skin. It is preferred that the external shield or skin be made from a conductive carbon material, however, other conductive materials are equally suitable. The conductive protrusion 63 is preferably made of steel. Other types of conductors may be used as well such as aluminum or copper. FIGS. 6A and 6B illustrate alternate orientations for the conductive protrusion 63. User preference may dictate which orientation is more desirable.

FIG. 7 illustrates an alternate embodiment of the electrical conductor-physical stimulator for use with the present invention. In this embodiment, the electrical conductor-physical stimulator 71 of the present invention is comprised of a finger tip end conductor having a circumference measuring 2½ inches at its attachment point 72. In this embodiment, only the conductive tip 73 is comprised of a conductive material. The main body of this conductor-physical stimulator is preferably not made from conductive material. It is cone-shaped and has a diameter of only 1¼ inches at its distal end 73. The electrical conductor-physical stimulator 71 is made of a stiff supportive structure. The conductive distal end 73 is preferably made of steel. Other types of conductors may be used as well such as aluminum or copper. The attachment point 72 may be internally threaded for engaging and securing to the distal end of the elongated member. The electrical connection to the generator may be made with a male/female plug located within a cavity formed between the conductor-physical stimulator which mates when the electrical conductor-physical stimulator is secured to the elongated member. Alternatively, the electrical connection may be made through the threading.

In the designs of the conductor-physical stimulator having a conductive external surface, the conductive external surface is electrically connected to a wire within the electrotherapy device for connection to the generator. In the designs with multiple electrical conductor-physical stimulators, wires for each of the separate electrical conductor-physical stimulators connect with corresponding wires in the electrotherapy device. The wires and plugs have not been shown in the illustration for the sake of clarity.

The conductive exterior shield of the remaining surface of the electrical conductor-physical stimulator 61 is made of a conductive black carbon. The protrusion 63 of the electrical conductor-physical stimulator is used for locating acupuncture and trigger points on a person's body. The protrusion 73 at the distal end of the electrical conductor-physical stimulator of FIG. 7 is used for locating acupuncture and trigger points on a person's body.

It is known that so called acupuncture and trigger points have increased conductivity and are particularly suitable for receiving electrotherapy. To find these points a micro-amp current is sent through the electrical conductor-physical stimulator and an electrical return path through a person's hand which is in contact with electrical conductor-physical stimulator 22 on the end of arcuate elongated member 20. The electrical conductor-physical stimulator 22 may be made of steel. When a patient begins treatment, he or she will first position the electrical conductor-physical stimulator 61 or 71 in the general vicinity of the treatment site on the patient's skin. The electrical conductor-physical stimulator will initially be positioned so that the protrusion 63 or 73 is located on the surface of a patient's skin in the general area of the treatment site. The patient will then switch the generator so that it will begin a seek function wherein the generator will produce a low-level electrical signal which is used in searching for the acupuncture or trigger point. The seek function of the generator examines the conductivity of various locations on the patient's skin (i.e. operating as an ohm meter) as the patient moves the electrical conductor-physical stimulator around on the surface in the general vicinity of the treatment site. The seek function examines the conductivity at each location and sounds an audible alarm when an acupuncture point is reached. This is a location which has increased conductivity or reduced resistance with respect to other areas. When the generator senses such an area and produces an alarm, the patient then begins electrical stimulation (i.e. high voltage galvanic current 5 to 1000 microamps at 30 pulses per second.) When physical stimulation is desired, the patient rotates the electrical conductor-physical stimulator 61 so that the protrusion 63 is no longer on the surface of the patient's skin but the conductor-stimulator 61 is still in contact with the skin. When using electrical conductor-physical stimulator illustrated in FIG. 7, no change in position is required and physical stimulation (massage may be performed without rotation).

The treatment regimen may include a combination of physical stimulation and electrotherapy. One significant advantage of this design is that the patient is able to locate an acupuncture or trigger point without having to remove the conductor-physical stimulator from the patient's skin. Previously, acupuncture or trigger point locators were used by a trained technician who would use separate devices for applying physical massage and electrotherapy. The present invention eliminates the need to remove the acupuncture or trigger point locator because the acupuncture or trigger point locator is actually contained within the electrical conductor-physical stimulator.

After a patient has applied the desired treatment at a particular location, the patient may again switch the electrical generator to the seek mode so that a new acupuncture or trigger point may be found. Once the new site is found, the patient will then switch the generator to apply the desired electrical stimulation or alternatively the patient may apply physical stimulation.

Figure 8:
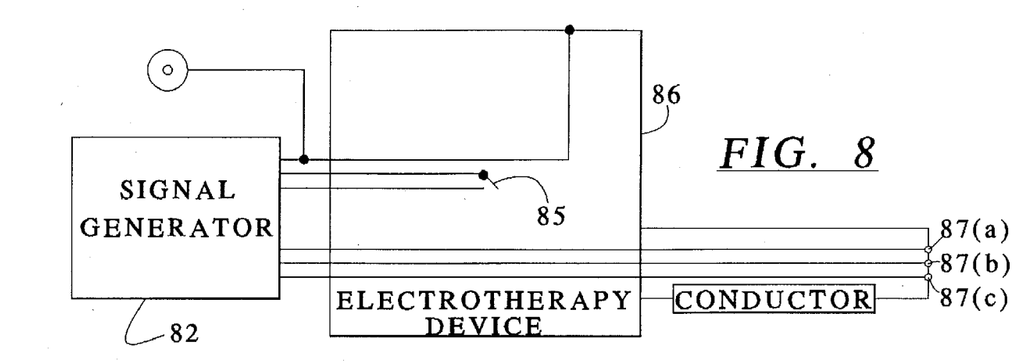
FIG. 8 is a schematic block diagram showing the connection of the electrotherapy device to the electrical generator.

FIG. 8 illustrates a schematic block diagram for the electrotherapy device of the present invention. An electric generator 82 generates electrical stimulation signals as well as acupuncture or trigger point locator signals for use with the electrotherapy device. A switch 85 located within the electrotherapy device 86 allows an individual to select between a seek mode and a stimulation mode. In the seek mode the generator provides a low level of output which is used in locating acupuncture or trigger points. When the generator is in the stimulation mode the generator provides electrical stimulation signals which are square wave pulses typically in the range of between 500 and 1000 microamps of current at 30 pulses per second on a negative charge. The pulses may be either all positive, all negative or alternating positive and negative. FIG. 8 illustrates a device wherein three physical stimulator/conductors provide electrical stimulation to a patient. Signal lines 87a, 87b and 87c are electrically isolated from one another and connect each of the conductors/physical stimulators. The generator may alternately provide the stimulation signal simultaneously on each of the signal lines 87(a), 87(b), and 87(c) or the generator may selectively provide the signal on a select signal line.

Figure 10A:
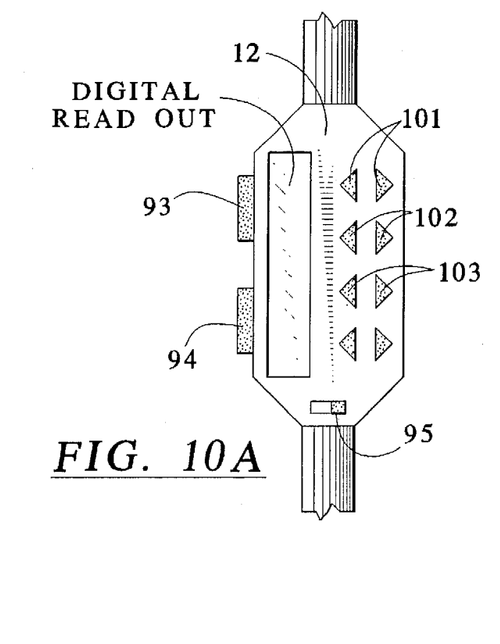
FIGS. 10A–10C illustrate plane view of the elongated member having the generator incorporated into the body of the elongated member.
Figure 10B:
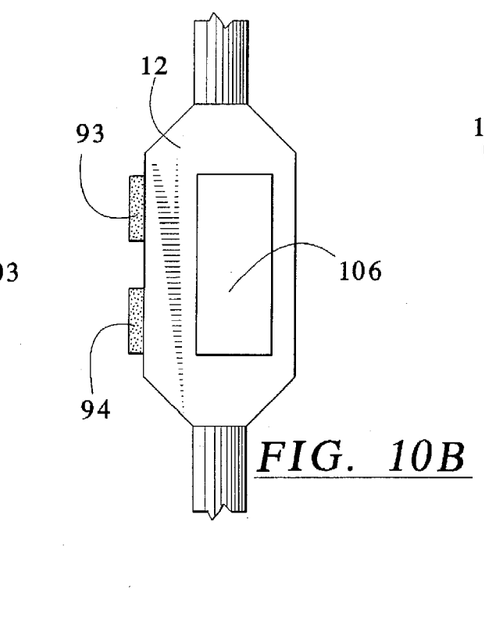
Figure 10C:
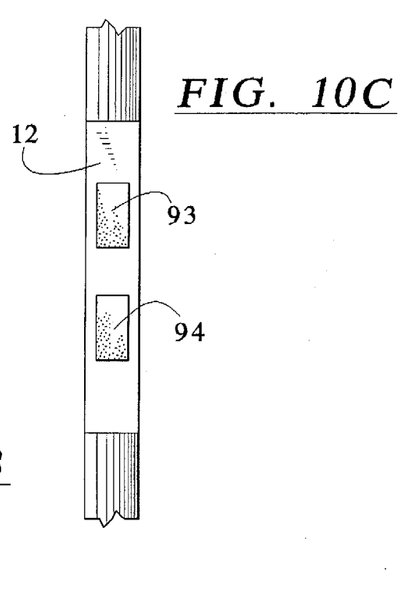

FIG. 9 illustrates an alternate embodiment of the present invention wherein the electrical generator is formed within the elongated member. In FIG. 9, the electrical generator 12 is centrally located within the elongated member, however, it is understood that other alternate locations for the generator within the elongated member may be used. FIGS. 10A-10C illustrate alternate views of the embodiment of the present invention illustrated in FIG. 9. FIG. 10A illustrates a top plane view showing the signal generator 12 located within the elongated member. A digital display readout which may be, for example, either an LCD or LED provides status information regarding the generator. The status information includes such things as whether it is in seek mode, therapy application mode, or whether the generator has low batteries. Other information may be provided on the display screen as well. The generator includes control buttons 93 and 94 for altering between seeking and providing electrical stimulation. Control button 93 sets the generator into a trigger point seek mode and button 94 sets the generator into a stimulation mode. Switch 95 is provided to turn the generator on and off. A battery save option senses when neither stimulation nor seeking has been performed for more than 5 minutes and will automatically shut the system down in order to conserve power. Volume switches are provided to adjust the volume of the electrical stimulation. Other controls 101, 102 and 103 respectfully adjust pulse rate and mode.

FIG. 10B illustrates a bottom plane view of the generator embodied within the electrotherapy device of the present invention. Battery cover 106 provides access to a common 9-volt battery which is used to provide power for the generator. Alternately, a rechargeable battery pack may be attached or stored within the generator for providing electrical power. It is also understood that the generator may be plugged into a wall socket low voltage power supply. FIG. 10C illustrates a side plane view of the generator of the present invention embodied within the electrotherapy device. A search button and scan button are illustrated therein.

The electrotherapy device of the present invention which is also known as the Stimucane can provide treatment for various stages of conditions through acute, sub-acute and chronic. The following description sets forth exemplary methods for treating various stages and conditions.

In the acute stage, tissues are inflamed, tender and hot. This limits many treatment options due to the high reactivity level of the tissues. A variety of these acute conditions can be treated with the Stimucane or electrotherapy device of the present invention. Most notably, these treatments can be given for myofacial active trigger points, muscle spasms, myositis, arthritis, and acupuncture points. An active trigger point such as a myofacial trigger point is a hyper-irritable locus within a taut band of skeletal muscle located in the muscular tissue and/or its associated fascia. The spot is painful on compression and can evoke characteristic referred pain and autonomic phenomena. Myofacial trigger points may be either active or latent. An active trigger point causes the patient pain. A latent trigger point is clinically silent with respect to pain, but may cause restriction of movement and weakness of the affected muscle. Active trigger points are likely in postural muscles of the neck, shoulder and pelvic girdles and the masticatory muscles. The upper trapezius, scalenus, sternocleidomastoid, levator scapula and quadratus lumborum muscles are very commonly involved. Additionally, muscle spasms which involve involuntary contraction of a muscle or a group of muscles attended by pain and interference with function such as myositis. Acute arthritis which involves inflammation of a joint or multiple joints with pain and stiffness causing disfunction can similarly be treated.

Chinese medical practitioners were aware of the art of treating these conditions through the use of needles which are used to pierce peripheral nerves to relieve pain. Today it is known that electrical stimulation of these points provides similar results. Studies indicate that many acupuncture points correspond to nerve innervation and trigger points. Fifty percent of all named acupuncture points are situated directly above major nerve trunks and most of the remaining acupuncture points have nerves within .5 centimeters of their location.

Treatment of these conditions commences with locating the acupuncture point and/or trigger points to reduce pain and deactivate myofacial active trigger points. A return path for the electrical current is provided through either the patient's hand attached to a conductor which provides the return path or alternately a skin placement electrode such as that shown as 40 in FIG. 4. The individual turns the signal to generator 12 to "on" and presses the search button, no. 101, which sets the generator into a seek mode that sets microamperage current through the trigger point locator probe. This may be the protrusion 63 from the electrical conductor-physical stimulator shown in FIGS. 6A and 6B, or alteratively, this may be the tip of the electrical conductor-or physical stimulator illustrated in FIG. 7. The probe is moved in a linear fashion no faster than 1 inch per second when the individual is using the device in a search mode for locating treatment sites. The area which is searched should be no larger than 4 inches by 4 inches. When a search in an area is complete, the patient may then move on to the next area if there is no success in finding the trigger point in the first area. The patient may then move on to the next area and begin searching again. When a trigger point is located, the generator will sound an audible tone. The probe should be located so that the audible tone is constant. If the probe is moved away from the trigger point the audible tone will cease. When the patient has located the treatment site the patient then switches the generator from a search mode to a stimulation mode by altering the position of the switch on the generator. The treatment current will range from 5 to 1000 micro-amps. Preferably the current is maintained just below the sensitivity level of the patient. The patient should not feel the current during the treatment cycle. When a condition is acute and painful, the patient will tolerate less current. The present invention allows a user to independently adjust the current from the generator so that a desired threshold is maintained.

As a patient's condition changes from acute to sub-acute, the patient will be able to tolerate a greater level of current before the patient is able to sense its presence. The present invention allows an individual to adjust the generator current to an appropriate level. Treatment should be maintained at a single site for up to 60 seconds. Upon completion of a treatment cycle at a first location, the patient then switches the generator again to the seek mode so that a new trigger point may be found and treated. During stimulation, the treatment may be accomplished with either a symmetrical or asymmetrical waveform. The current type may be either faradic, galvanic, interrupted galvanic, low voltage or high voltage. Experimentation will determine which is the most effective type for a given patient condition.

Other types of conditions may also be treated including, for example, sub-acute conditions. The present invention may also be used for providing treatment of these sub-acute conditions such as, myofacial active trigger points, chemical muscle holding, muscle contusion and muscle strain. In the sub-acute stage, an active trigger point has a lower temperature and is less tender and toned than that of an acute stage. Chemical muscle holding also occurs during this stage which is evident from an ache in the muscle which is as if the muscle had been worked out hard during the preceding day. Chemical muscle holding is the result of a muscle spasm which prevents the release of metabolites and fluids. Muscle contusions or strains may also be present during this stage.

Treatment during the sub-acute condition begins with the acupuncture or trigger point locator which is used to find the trigger points as noted above. The conductor-physical stimulators are then used for providing electrical stimulation to increase blood flow and reduce edema. This helps the healing process so that muscle function can return to normal. As noted previously a ground or electrical signal return path is first provided preferably through a skin surface electrode. It is desirable to locate the skin surface electrode approximately no more than 12 inches from the treatment site. The larger the surface area of the contact, the better tolerance the patient will have for higher levels of electrical stimulation.

After selecting a particular electrode conductor-physical stimulator such as those illustrated in FIGS. 2, 3 and, 6A, 6B and 7 a sponge cover such as that shown in FIG. 5 is soaked in a saline solution to increase conductivity. Alternately, a conductive gel may be used to increase the conductivity. The user then turns the signal generator to the "on" position and adjusts the level of stimulation so that a comfortable level of stimulation is achieved. It is preferred that the patient maintain the conductor-physical stimulators in contact with the surface of the patient's skin so that charge does not accumulate and cause a painful discharge or "bite". The conductor-physical stimulator should be moved in a small circular motion having a rate of motion which is no more than 4 inches per second. The amount of electrical stimulation current which a patient will tolerate depends on the reactivity level of the patient's tissues. Some areas may be more sensitive than others. The patient should adjust the electrical signal level to be the highest within a range which is comfortable. The treatment time should be generally from 5 to 10 minutes. A variety of pulse types, magnitudes and durations may be used. Experimentation will identify the most appropriate electrical signals for use with the present invention.

Other musculoskeletal conditions not mentioned above can also be treated with the device and methods of the present invention. The decision as to the most appropriate treatment and the ability of the patient to carry out the treatment will be made by the individual's health care practitioner.

The above-mentioned conditions will also benefit from deep pressure massage. The Stimucane or electrotherapy device of the present invention can simultaneously provide physical stimulation through the conductor-physical stimulator heads while also providing the selected electrical stimulation. Thus the conductor is referenced as a conductor-physical stimulator. An individual, may choose to self administer physical stimulation exclusive for the treatment of muscle tension, headaches, latent trigger points, etc.

The present invention is subject to many variations, modifications and changes in detail. It is intended that all matter described throughout the specification and shown in the accompanying drawings be considered illustrative only. Accordingly, it is intended that the invention be limited only by the spirit and scope of the appended claims.

We claim as our invention:

1. An electrotherapy device comprising: an elongated member having a length defined between a first end and a second end with a uniform cross-sectional dimension between the first end and the second end;

a conductor-physical stimulator connected to the first end of the elongated member wherein the conductor-physical stimulator has a cross-sectional dimension greater than a uniform cross-sectional dimension; and an electrical signal generator electrically connected to the conductor-physical stimulator and further electrically connected to the elongated member at a point intermediate the first end and the second end.

2. The electrotherapy device of claim 1 further comprising:

a plurality of conductor-physical stimulators attached to the first end of the elongated member.

3. The electrotherapy device of claim 2 further comprising:

a corresponding plurality of electrical connections between corresponding separate outputs of the electrical generator and the plurality of conductor-physical stimulators.

4. The electrotherapy device of claim 1 further comprising:

three conductor-physical stimulators attached to the first end of the elongated member.

5. The electrotherapy device of claim 1 further comprising:

a protrusion extending from a surface of the conductor-physical stimulator.

6. The electrotherapy device of claim 1 further comprising:

a sponge secured to a surface of the conductor-physical stimulator.

7. The electrotherapy device of claim 1 wherein the electrical signal generator is manually adjustable.

8. The electrotherapy device of claim 1, wherein the electrical signal generator has a programmable capability.

9. The electrotherapy device of claim 1 further comprising:

a skin placement electrode attached to the electrical signal generator.

10. The electrotherapy device of claim 1 further comprising:

an aluminum external surface on the conductor-physical stimulator.

11. A method of massaging and providing electrical electrotherapy to a patient, the method comprising the steps of:

a) providing an elongated member having a length defined between a first end and a second end with a uniform cross-sectional dimension between the first end and the second end and further having an electrical conductor-physical stimulator on the first end of the elongated member wherein the electrical conductor-physical stimulator has a cross-sectional dimension greater than the uniform cross-sectional dimension;

b) maneuvering the electrical conductor-physical stimulator on the first end of the elongated member across a skin surface of the patient;

c) applying a trigger point locator current to the electrical conductor-physical stimulator to locate a first trigger point;

d) simultaneously massaging a first located trigger point with the electrical conductor-physical stimulator while applying a stimulation current through the electrical conductor-physical stimulator.

12. An electrotherapy device comprising:

an elongated member;

a conductor-physical stimulator connected to a first end of the elongated member; and an electrical signal generator electrically connected to the conductor-physical stimulator wherein the conductor-physical stimulator further comprises a protrusion extending from a surface of the conductor-physical stimulator.

13. An electrotherapy device comprising:

an elongated member;

a conductor-physical stimulator connected to a first end of the elongated member; and an electrical signal generator electrically connected to the conductor-physical stimulator; and a sponge secured to a surface of the conductor-physical stimulator.

14. An electrotherapy device comprising:

an elongated member;

a conductor-physical stimulator connected to a first end of the elongated member; and a programmable electrical signal generator electrically connected to the conductor-physical stimulator.

15. An electrotherapy device comprising:

an elongated member;

a conductor-physical stimulator connected to a first end of the elongated member;

an electrical signal generator electrically connected to the conductor-physical stimulator; and an aluminum external surface on the conductor-physical stimulator.

* * * * *